(12) United States Patent
Pollock

(10) Patent No.: US 7,860,571 B2
(45) Date of Patent: Dec. 28, 2010

(54) PAIN RELIEF DEVICE

(76) Inventor: Frederick William Pollock, 9936, Oakridge Rd. S.W., Calagry, Alberta (CA) T2V 4A5

( * ) Notice: Subject to any disclaimer, the term of this patent is extended or adjusted under 35 U.S.C. 154(b) by 506 days.

(21) Appl. No.: 12/061,018

(22) Filed: Apr. 2, 2008

(65) Prior Publication Data
US 2008/0221639 A1    Sep. 11, 2008

Related U.S. Application Data

(63) Continuation of application No. 10/419,300, filed on Apr. 22, 2003, now abandoned.

(51) Int. Cl.
*A61N 1/00* (2006.01)
(52) U.S. Cl. .......................................................... 607/46
(58) Field of Classification Search .................. 607/46; 600/548
See application file for complete search history.

(56) References Cited

U.S. PATENT DOCUMENTS

| | | |
|---|---|---|
| 524,664 A | 8/1894 | Brewster |
| 563,016 A | 6/1896 | Collicott |
| 2,661,744 A | 12/1953 | Browner |
| 3,386,445 A | 6/1968 | McDonald |
| 3,898,981 A | 8/1975 | Basham |
| 3,978,378 A | 8/1976 | Tigner et al. |
| 4,061,897 A | 12/1977 | Thykeson |
| 4,323,073 A | 4/1982 | Ferris |
| 4,398,545 A | 8/1983 | Wilson |
| 4,534,886 A | 8/1985 | Kraus et al. |
| 4,616,654 A | 10/1986 | Bacchelli |
| 4,895,160 A | 1/1990 | Reents |
| 4,934,383 A | 6/1990 | Glumac |
| 4,940,060 A * | 7/1990 | Gu et al. ..................... 600/548 |
| 5,224,928 A | 7/1993 | Sibalis et al. |
| 5,374,283 A | 12/1994 | Flick |
| 5,423,874 A | 6/1995 | D'Alerta |
| 5,653,741 A | 8/1997 | Grant |
| 5,743,494 A | 4/1998 | Giamati et al. |
| 6,059,310 A | 5/2000 | Buss |
| 6,408,211 B1 | 6/2002 | Powell |

FOREIGN PATENT DOCUMENTS

| | | |
|---|---|---|
| CA | 2414398 | 6/2004 |
| EP | 0367320 | 5/1990 |
| EP | 0774271 | 5/1997 |

* cited by examiner

*Primary Examiner*—George Manuel
(74) *Attorney, Agent, or Firm*—Maxey Law Offices, PLLC; Stephen Lewellyn

(57) ABSTRACT

The Pain relief device used to relieve pain and promote faster healing in the bodies of humans and animals safely. A positive electrode touches the skin at the site of an injury and a negative electrode completely shielded with insulation is place on the skin at a spaced distance form the positive electrode. A low voltage direct current power source supplies a positive voltage to the positive electrode and a negative voltage to the negative electrode. Electrical stimulation occurs harmlessly, because the shielded negatively charged electrode or insulated pad, being an insulated sheet of aluminum foil produces an electric field in the body that is strong enough to cause a current to flow into the body at the site of the positive electrode. However, no current can flow at the site of the negative electrode because it is insulated and therefore no burns to the skin.

3 Claims, 3 Drawing Sheets

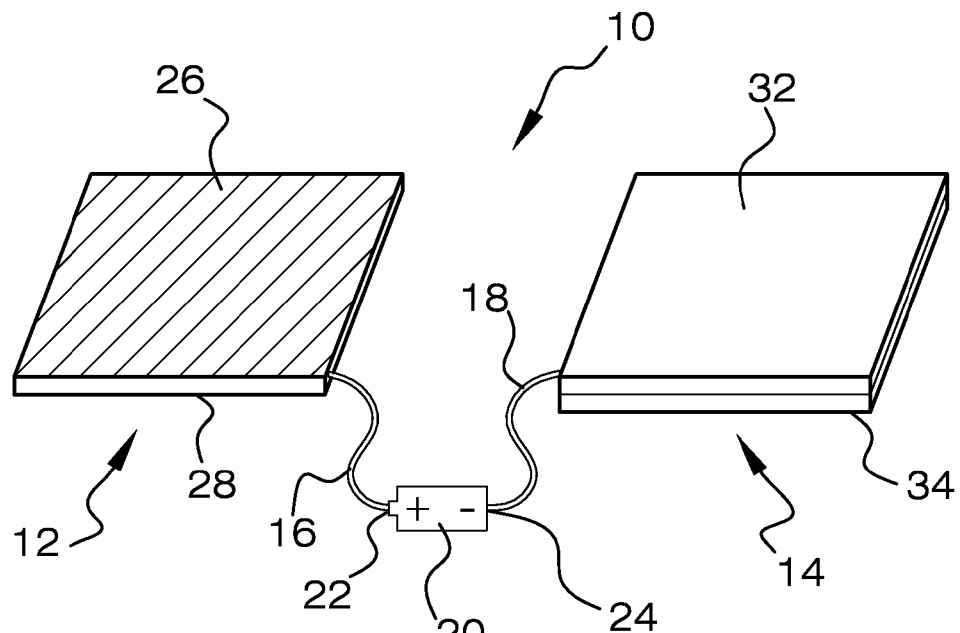
FIG. 1
FIG. 2
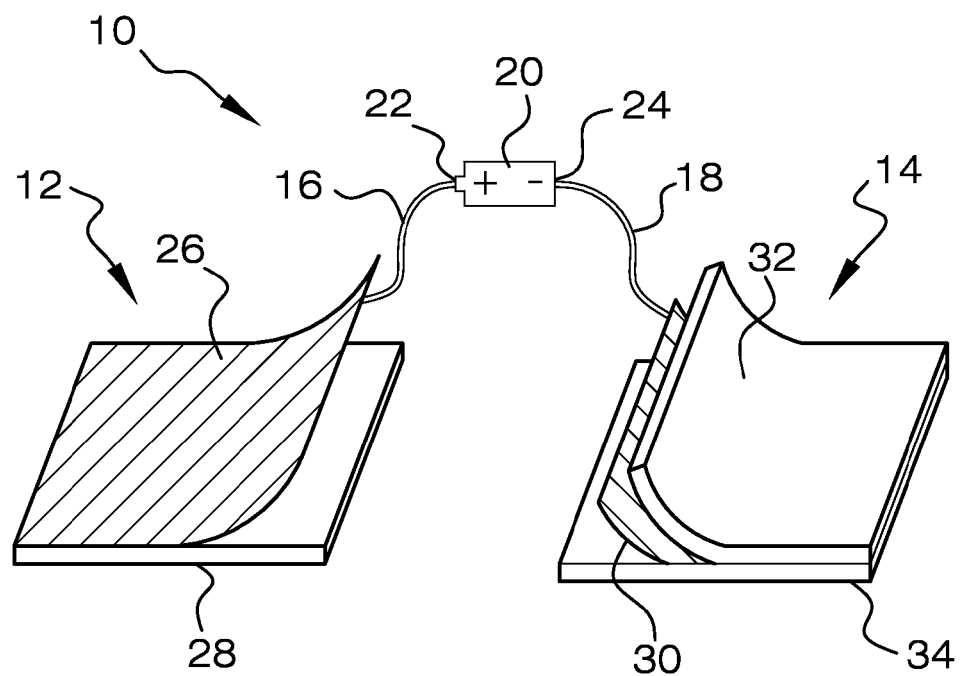

PAIN RELIEF DEVICE

CROSS-REFERENCE TO RELATED APPLICATIONS

This application claims the benefit of U.S. application Ser. No. 10/419,300, filed Apr. 22, 2003, the entire of which is incorporated herein by reference.

FIELD OF THE INVENTION

The present invention relates generally to a pain relief device, and more particularly, relating to electrical stimulus pain relief device and method of the same.

BACKGROUND OF THE INVENTION

Pain relieving devices are known in the art. However, a new and improved pain relief device of a new construction and method of the same is needed.

SUMMARY OF THE INVENTION

The pain relief device creates a type of electro-therapy for people who have a sore joint or muscle and want relief from pain. The device consists of two pad-type electrodes, or pads, wired to a DC power source such as a battery; one pad to the positive (+) pole and the other pad to the negative (−) pole. The pads are broad, flat, and thin, and could be any shape or size above a square inch in area, (See FIG. 1A) and are placed flat against the body. One pad, the conducting pad, is placed on the skin of the body at the site of the injury. This pad consists of a single sheet of aluminum foil or other like material only, and this sheet of aluminum foil is large enough to completely cover the area of the injury. This sheet of aluminum foil is converted into a flat sheet like electrode after it is electrically connected to the positive (+) pole of a low voltage DC power source by insulated electrical wire. When on the body, in full contact with the skin of the injured area, and wired as above, the positive (+) charge of the DC power source is distributed equally throughout the sheet of aluminum foil as aluminum is an excellent conductor of electricity. Where the aluminum foil, thus charged up, is in contact with the skin, the positive (+) charge of the aluminum foil sets up a positive charge on the skin around the site of the injury. This affect, and how it is used will be explained below following the description of the insulated pad.

The insulated pad is also a flat sheet like electrode such as a sheet of aluminum foil and has roughly the same area or is larger than the above mentioned conducting pad's conductive sheet. This electrode of aluminum foil is hard wired to the negative (−) pole of the same DC power source as the conducting pad above. Besides the polarity differences in wiring, to this point, the electrodes being used in the insulated pad and the conducting pad are basically the same, being flat sheets of aluminum foil with the same general shape and area. The insulated pad is fabricated by taking the negatively (−) charged, aluminum foil electrode and completely covering it, on both sides, of the aluminum foil sheet, by insulation. The flat, aluminum foil sheet electrode becomes completely shielded electrically, in that no current can pass from the electrode within the insulated pad to the outside of the insulated pad, thus earning its name. When the insulated pad is placed on the skin of the body, it produces a negatively (−) charged electric field in the body centered at the location of the insulated pad and radiating outward through the body.

When these two pads, wired as above, are placed on the body simultaneously, an electric field is set up flowing through the body from the positively (+) charged pad to the negatively (−) charged pad. At the location of the insulated pad, no current can flow from the body to the negative (−) electrode within as it is completely electrically insulated. The negative (−) electric field created by the electrode will still, however, flow through the insulation and flow throughout the body. When the positively (+) charged conducting pad is placed on the skin on the injured region of a body when it is being charged by an insulated pad from the opposite side of the body from the injury, there is an interaction of the electric fields at the site of the conducting pad. The excess positive (+) charge build up in the conducting pad is drawn to the negative (−) field in the body produced by the insulated pad. When this negatively (−) charged field is set up in the body, charged particles in the body will be attracted to the appositely charged electrodes, or pads. Although none of these charged particles can pass from the body through the skin into the insulated pad, there is nothing to stop the appositely charged particles from passing through the skin of the body at the location of the conducting pad as it is a bare aluminum foil electrode on exposed, bare, skin. This minute flow of current at the site of the conducting pad creates an environment that relieves pain and promotes faster healing in the joint or muscle being treated.

The effectiveness of the device will vary depending on the voltage used, the surface area of the pads, and the placement of the pads on the body, all which will affect the electric field set up between the two pads through the body. The best results occur when the pads arc as close as they can be to each other on the body while being on the opposite side of the body from each other. The electric field is perpendicular to the surface created by the flat pads. Having the pads directly facing each other from opposite sides of the body is ideal. The reason for this is because we are trying to focus the electric field so that it flows through the location of the injury to maximize the affect of the conducting pad.

A large insulated pad placed on the stomach can be used as alternative way to create the negative (−) field in the body. From the stomach, it will cause a negatively (−) charged electric field to flow throughout the whole body. If the conducting pad is placed elsewhere on the body, (back, knee, elbow, hip, shoulder, etc.), to treat an injury, the electric field produced by the insulated pad on the stomach will produce an electric current in the conducting pad and produce a positive therapeutic affect on the injury being treated.

The voltages being used for all these devices has ranged from 0.0 volts up to 7.0 volts DC. Devices using 1.5-3.0 volts are universally well tolerated and produce excellent results.

Once the pads are positioned on the body as described above they should be left in this manner as long as is possible and comfortable to the subject, until the pain goes away. FIG. 3A, demonstrates the placement, configuration, and general dimensions of a device designed to treat lower back pain as one of many examples.

To achieve these and other advantages, in general, and in one aspect, a method of relieving pain through electric stimulation is provided. The method includes contacting the skin surface of a patient with an electrically conductive pad and contacting the skin surface of a patient at a spaced location from the electrically conductive pad with an electrically insulated pad having an electrically conductive core that is electrically insulated against electrical current flowing therefrom into the skin surface. Applying a positive voltage to the electrically conductive pad from a power source and applying a negative voltage to the electrically conductive core from the power source. Generating a negative electric field in the skin surface about said electrically insulated pad and causing electrical current to flow from said electrically conductive pad towards said negative electric field, thereby providing therapeutic relief to the user.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The accompanying drawings, which are included to provide further understanding of the invention and are incorporated in and constitute a part of this specification, illustrate preferred embodiments of the invention and together with the description serve to explain the principles of the invention, in which:

FIG. 1 is a perspective view of the pain relief device constructed in accordance with the principles of the present invention;

FIG. 2 is a perspective view of the pain relief device, illustrating the structure of the conducting pad and the insulated pad;

DETAILED DESCRIPTION OF THE INVENTION

Figure 3A:
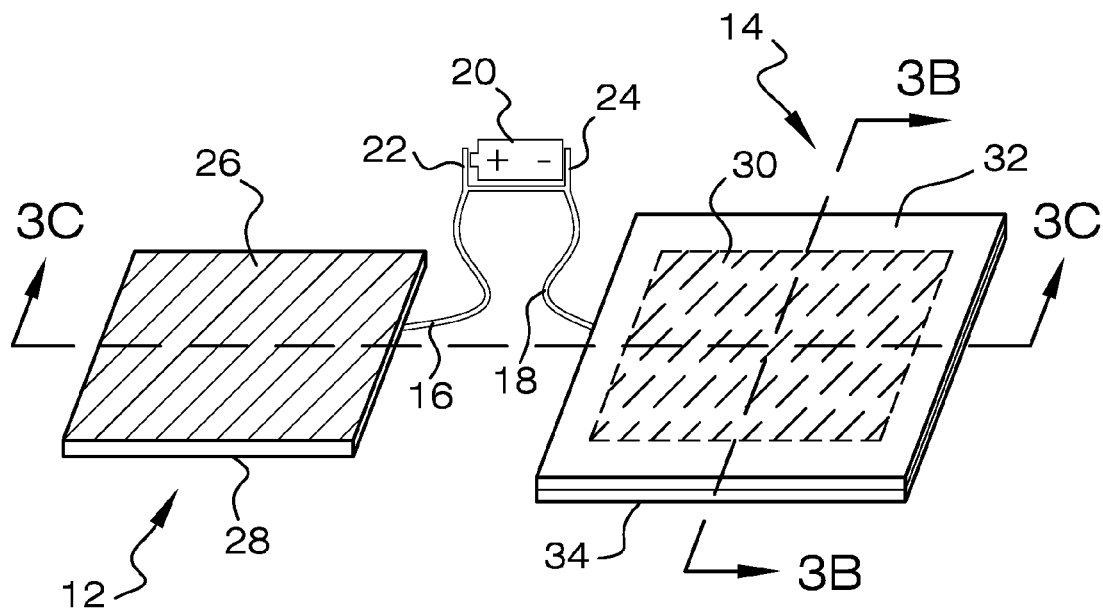
FIG. 3A is a perspective view of the pain relief device, illustrating the conductive material of the insulated pad.

Reference will now be made in detail to the preferred embodiments of the present invention, examples of which are illustrated in the accompanying drawings.

Referring now to the drawings, reference numeral 10 generally designates a pain relief device of the present invention. The device creates a type of electro-therapy for humans or animals for safely relieving pain and speeding recovery of an injury. The injury may be a sore joint or muscle. As shown in FIG. 1 the device includes two pad-type electrodes one being a thin flexible conducting pad 12, the second being a thin flexible insulted pad 14, a first insulated wire 16, a second insulated wire 18 and a low voltage direct current (DC) power source 20 having a positive (+) pole 22 and a negative (−) pole 24. The low voltage DC power source 20 may be any type of battery or multiple batteries, such as, conventional A, AA, AAA type batteries having a positive (+) pole 22 and a negative (−) pole 24. The voltages being used for the device range from 0.0 volts up to 7.0 volts DC as an example the power source 20 can provide 1.5 to 7.0 volts. When in use both the conducting pad 12 and the insulated pad 14 will have the same voltage applied to them.

Figure 3B:
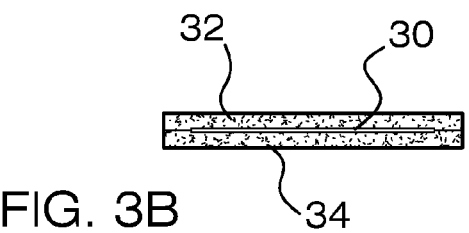
FIG. 3B is a cross sectional view of the pain relief device taken along line 3B-3B, showing the core and insulation layers of the insulated pad.
Figure 3C:
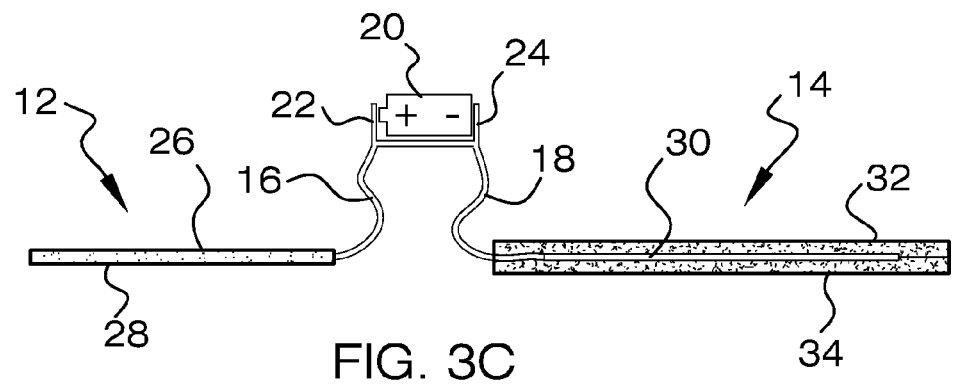
FIG. 3C is a cross sectional view of the pain relief device taken along the line 3C-3C, showing the structure of the insulated pad and conductive pad.
Figure 4:
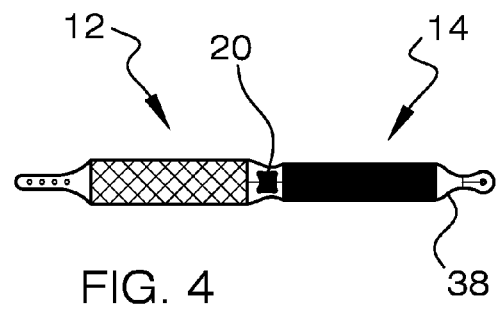
FIG. 4 is a top plan view of the pain relief device, illustrating the pain relief device constructed as a belt in accordance with the principles of the present invention.

Referring to FIGS. 1-4, the conducting pad 14 includes a thin flexible sheet of conductive material 26 and a layer of insulation 28 covering one side of the conductive material and leaving one side of the conductive material exposed. The layer of insulation 28 is used for structurally supporting and strengthening the sheet of thin flexible conductive material 26. The conductive material 26 of the conducting pad 14 is attached to the low voltage power source 20 by the first insulated wire 16. One end of the first insulated wire 16 is connected to the conductive material 26 of the conducting pad 12 and a second end of the wire is connected to the positive (+) pole 22 of the power source 20.

Additionally, FIGS. 1-4 show the insulated pad 14 including a core 30 made of a thin flexible sheet of conductive material, a first layer of insulation 32 covering one side of the core and a second layer 34 of insulation covering a second side of the core. The negative pole 24 of the same power source 20 that is connected to the conducting pad 12 is connected to the insulated pad 14 by the second insulated wire 18. One end of the second insulated wire 18 is connected to the core 30 of the insulated pad 14 and a second end of the wire connects to the negative (−) pole 24 of the power source 20. The second insulted wire 18 is connected to the core 30 of the insulated pad 14 in such a way that no conductive material or electrical contact is exposed.

The size and shape of the conducting and insulated pads 12, 14 may be of any size and shaped which covers the injured part of the body and may even be a point electrode. The conductive material 26 and core 30 for both the conducting pad 12 and the insulated pad 14 is preferably made of aluminum but may be any type of thin flexible conductive material such as copper, silver, gold, platinum, or any other alloy of these or other metals shaped into a foil or screen or multiple thin layers. The layers of insulation 28, 32, 34 used for both the conducting and insulation pads 12, 14 may be any flexible insulating material such as vinyl, latex, plastic, duct tape, fabric, cloth, leather, paper or felt.

The conducting pad 12 is placed on the skin of the body at the site of the injury. The conducting pad 12 is sized large enough to completely cover the area of the injury. The exposed side of the conducting pad 12 is placed in direct contact on the skin so the exposed conductive material 26 is in direct contact with the skin of the body at the site of the injury. The sheet of conductive material 26 is converted into a flat sheet like electrode after it is electrically connected to the positive (+) pole 22 of the power source 20 by the first insulated wire 16. When on the body, in full contact with the skin of the injured area, and wired as above, the positive (+) charge of the power source 20 is distributed equally throughout the sheet of conductive material 26. Where the conductive material 26, thus charged up, is in contact with the skin, the positive (+) charge of the conductive material 26 sets up a positive charge on the skin around the site of the injury.

The insulated pad 14 is placed on the skin of the body at a position opposite side of the injury and the conducting pad 12. The insulated pad 14 is roughly the same size or is larger than the conducting pad 12. If a location opposite the placement of the conducting pad 12 is unavailable or difficult for the placement of the insulating pad 14, the device will also work if the insulated pad is placed against the skin of the abdomen even though the injury may be the shoulder, neck etc. The devices will work as long as the conductive material 26 of the conducting pad 12 is connected to the positive (+) pole 22 of power source 20 and is in contact with the injured area and the core 30 of the insulated pad 14 is connected to the negative (−) pole 24 of the same power source and the insulated pad 14 is placed on another part of the body preferably but not necessarily opposite to the placement of the conducting pad. The core 30 of the insulated pad is converted into a flat sheet like electrode after it is electrically connected to the negative (−) pole 24 of the power source 20 by the second insulated wire 18. When the insulated pad 14 is placed on the skin of the body, it produces a negatively (−) charged electric field in the body centered at the location of the insulated pad and radiates outward through the body. No current can flow at the site of the negatively charged core 30 of the insulated pad 14 because it is insulated and therefore the skin of the body can does not burn.

When the conducting pad 12 and insulated pad 14, wired as above, are placed on the body simultaneously, an electric field is set up flowing through the body from the positively (+) charged conducting pad to the negatively (−) charged insulated pad. At the location of the insulated pad 14, no current can flow from the body to the negatively charged core 30 within, as it is completely electrically insulated. The negative (−) electric field created by the core 30 will still, however, flow through the insulation 32, 34 and flow throughout the body. When the positively (+) charged conducting pad 12 is placed on the skin on the injured region of a body when it is being charged by an insulated pad 14 from the opposite side of the body from the injury, there is an interaction of the electric fields at the site of the conducting pad. The excess positive (+) charge build up in the conducting pad 12 is drawn to the negative (−) field in the body produced by the insulated pad 14. When this negatively (−) charged field is set up in the body, charged particles in the body will be attracted to the oppositely charged electrodes, or pads 12, 14. Although, none of these charged particles can pass from the body through the skin into the insulated pad 14, there is nothing to stop the oppositely charged particles from passing through the skin of the body at the location of the conducting pad 12 as it is a bare conducting material on exposed, bare, skin. This minute flow of current at the site of the conducting pad 12 creates an environment that relieves pain and promotes faster healing in the joint or muscle being treated.

The effectiveness of the device will vary depending on the voltage used, the surface area of the pads 12, 14 and the placement of the pads on the body, all which will affect the electric field set up between the two pads through the body. The best results occur when the pads 12, 14 are as close as they can be to each other on the body while being on the opposite side of the body from each other. The electric field is perpendicular to the surface created by the flat pads 12, 14. Having the pads 12, 14 directly facing each other from opposite sides of the body is ideal. The reason for this is because we are trying to focus the electric field so that it flows through the location of the injury to maximize the affect of the conducting pad 12.

Additionally, a large insulated pad 14 placed on the stomach can be used to create the negative (−) field in the body. From the stomach, it will cause a negatively (−) charged electric field to flow throughout the whole body. If the conducting pad 12 is placed elsewhere on the body, (back, knee, elbow, hip, shoulder, etc.), to treat an injury, the electric field produced by the insulated pad 14 on the stomach will produce an electric current in the conducting pad and produce a positive therapeutic affect on the injury being treated.

Figure 5:
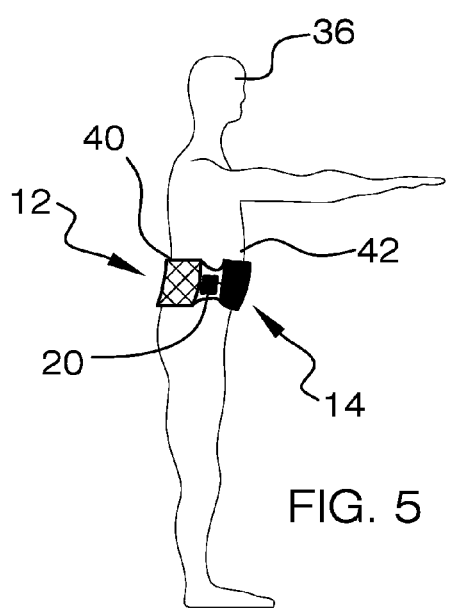
FIG. 5 is a side elevation view of the pain relief device, illustrating the belt in use on a human.
Figure 6:
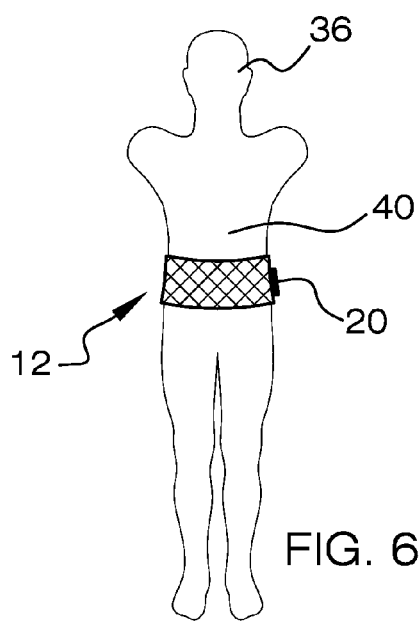
FIG. 6 is a rear elevation view of the pain relief device, illustrating the placement of the conducting pad and belt attached to a human.
Figure 7:
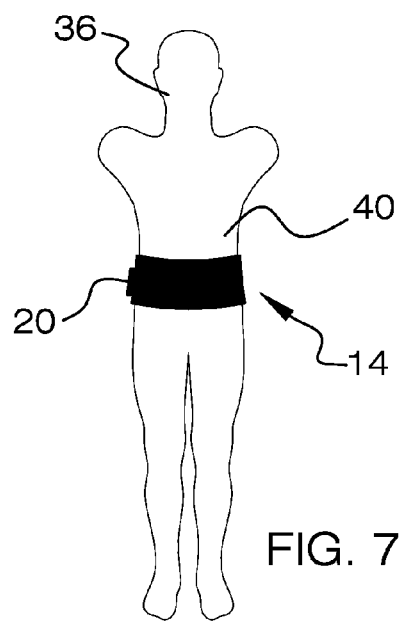
FIG. 7 is a front elevation view of the pain relief device, illustrating the placement of the insulated pad and belt attached to a human.

Once the pads 12, 14 are positioned on the body as described above they should be left in this manner as long as is possible and comfortable to the subject, until the pain goes away. FIGS. 4-7 demonstrates the placement, configuration, and general dimensions of a device designed to treat lower back pain as one of many examples.

As an example, if the lower back is injured and one wishes to treat it with this device using this principle. The pads 12, 14 of the device and the electrical wiring would be constructed and put together exactly as described and seen in FIG. 1-3C. This example is for a 200 LB. human 36 of average height, the x-y and x'-y' dimensions of the respective pads 12, 14 shown in FIG. 4, would be 5 in. by 14 in. for both the conducting material 26 of the conducting pad 12 and the core 30 of the insulated pad 14. This particular device uses two AA batteries in a battery pack wired in series providing approximately 3 volts DC. This device can be affixed easily to the human 36 if the pads 12, 14 and power source 20 wired as above are held in place by a wide belt 38, shown in FIG. 4-7. The exposed conductive material 26 of the conducting pad 12 is placed against the skin of the lower back 40 while the insulated pad 14 is placed against the skin of the stomach or abdomen 42 as in FIGS. 5-7. This configuration will relieve pain in the lower back and promote faster healing. Rather than using a separate belt, a large belt made from the same type of insulating material can be used instead of separate pieces of insulation for each pad 12, 14.

Devices based on this principal have been adapted to ease pain and speed healing in the knee, shoulder, wrist, elbow, ankle, feet, and neck with positive results. Indeed any injured or strained muscle or joint in the body could benefit from this treatment. It has been used to treat the sore hip of a dog as well using a metal brush type adapter for the conducting pad 12 with each tooth of the brush charged with the same voltage used in the insulated pad 14. The brush is used so that the fur on the animal can be penetrated so that the electrodes in the brush are in contact with the animal's skin. There is no reason why this technology wouldn't work just as well on any other mammal.

A number of embodiments of the present invention have been described. Nevertheless, it will be understood that various modifications may be made without departing from the spirit and scope of the invention. Accordingly, other embodiments are within the scope of the following claims.

What I claim as my invention and discovery is:

1. A method of relieving pain and promoting recovery of a body injury, comprising the steps of:
   providing an electrically conductive pad having an exposed conductive material;
   connecting said conductive material to a positive pole of a low voltage power source;

providing an electrically insulated pad having a core of a conductive material that is completely electrically insulated;

connecting said core to a negative pole of said low voltage power source;

contacting said exposed conductive material of said electrically conductive pad to the bare skin of a patient;

contacting said electrically insulated pad at a spaced distance from said exposed conductive material to the bare skin of a patient;

applying a positive voltage to said exposed conductive material from said power source;

applying a negative voltage to said core from said power source;

generating an negative electric field about said electrically insulated pad;

causing current to flow from said positively charged exposed conductive material towards said negative electric field; and preventing current flow between said bare skin and said electrically insulated pad.

2. The method of claim 1, further comprising the step of:
positioning said conductive pad and said insulated pad on opposite sides of a body portion of the patient.

3. A method of relieving pain through electric stimulation, comprising the steps of:

contacting the skin surface of a patient with an electrically conductive pad;

contacting the skin surface of a patient at a spaced location from said electrically conductive pad with an electrically insulated pad having an electrically conductive core that is electrically insulated against electrical current flowing therefrom into the skin surface;

applying a positive voltage to said electrically conductive pad from a power source;

applying a negative voltage to said electrically conductive core from said power source;

generating a negative electric field in the skin surface about said electrically insulated pad; and causing electrical current to flow from said electrically conductive pad towards said negative electric field.

* * * * *